United States Patent [19]

Plata et al.

[11] Patent Number: 5,164,196

[45] Date of Patent: Nov. 17, 1992

[54] CROTOXIN COMPLEX AS CYTOTOXIC AGENT

[75] Inventors: Guillermo J. H. Plata, Maracaibo-Zulia, Venezuela; Luis A. Costa, Buenos Aires; Carlos M. Coni, La Rioja, both of Argentina; Juan C. Vidal, Cambridge, Mass.

[73] Assignee: Ventech Research, Inc., Cambridge, Mass.

[21] Appl. No.: 460,508

[22] Filed: Jan. 3, 1990

Related U.S. Application Data

[63] Continuation-in-part of Ser. No. 51,942, May 19, 1987, abandoned.

[51] Int. Cl.$^5$ ............................................. A61K 35/58
[52] U.S. Cl. ...................................... 424/548; 514/2; 514/21; 530/856
[58] Field of Search ..................... 424/542; 514/2, 21; 530/856, 413-419

[56] References Cited

U.S. PATENT DOCUMENTS

| | | | |
|---|---|---|---|
| 4,341,762 | 7/1982 | Haast | 424/98 |
| 4,610,879 | 9/1986 | Markland, Jr. et al. | 424/98 |
| 4,774,318 | 9/1988 | Marquardt et al. | 533/324 |

OTHER PUBLICATIONS

Gil, Antitumor Drug; CA105:165008 (1986).
Hendon et al., BA68(9):57778 (1979).
Wu et al., Journal of Chromatography 259:375-377 (1983).
Braganca, et al., *Biochim. Biophys. Acta*, 136:508-520 (1967).
Takechi, et al., *Naturwissenschaften* 58. Jg., Heft 6:323-324 (1971).
Cotte, et al., *Toxicon* 10:157-161 (1972).
Rübsamen, et al., *Naunyn-Schmiedeberg's Arch. Pharmac.* 270:274-288 (1971).
Hendon, et al., *PNAS* 68:1560-1563 (1971).
Aird, et al., *Arch. Biochem. Biophys.* 249:296-300 (1986).
Habermann, et al., *Toxicon* 16:19-30 (1978).
Breithaupt, et al., *Eur. J. Biochem.* 49:333-345 (1974).
Aird, et al., *Biochemistry*, 24:7054-7058 (1985).
Jeng, et al., *PNAS*, 75:600-604 (1978).
Bon, et al., *Eur. J. Biochem.*, 99:471-481 (1979).
Volwerk, et al., *Biochemistry*, 13:1446-1454 (1974).
Wallach, Chapter 6, *Biological Membranes*, Chapman, ed., Academic Press, New York, 1973.

*Primary Examiner*—Douglas W. Robinson
*Assistant Examiner*—Jean C. Witz
*Attorney, Agent, or Firm*—Scully, Scott, Murphy & Presser

[57] ABSTRACT

The present invention provides a stable composition of matter based on the cytotoxic activity of a basic phospholipase $A_2$ of molecular weight 14,500 and isoelectric point 9.6-9.7 (crotoxin B) isolated from the venom of *Crotalus durissus terrificus* which in complex with a specific, non-enzymatic, peptide of molecular weight 9,500 and isoelectric point 3.5-3.7 (crotoxin A) displays a preferential cytotoxic activity against various types of tumor cells. When administered parenterally in an acceptable vehicle and in pharmacologically efficient amounts to animals and humans the complex is useful in the treatment of malignant tumors in advanced stages. The method for purification of the active components, the preparation in a pharmacologically acceptable form, and the method of therapeutic use of the present composition of matter are also disclosed.

7 Claims, No Drawings

CROTOXIN COMPLEX AS CYTOTOXIC AGENT

This application is a continuation-in-part of our application, Ser. No. 07/051,942, filed May 19,1987, now abandoned.

TECHNICAL FIELD OF THE INVENTION

This invention refers to pharmaceutical compositions useful for the treatment of carcinomas, and also applicable as analgesics, which comprise as therapeutic agent the crotoxin complex obtained from the crude Crotalus durissus terrificus venom in a pharmacologically acceptable vehicle. The invention also refers to methods for the treatment of carcinomas by administering pharmacologically efficient amounts of said composition.

DESCRIPTION OF THE PRIOR ART

The analgesic effect of snake venoms has been known since antiquity and several authors have pointed out the rattlesnake venoms in the treatment of trigeminal neuralgias, tabetic and tumoral algies. In the cases of tumoral the patients could be maintained without the administration of morphine in 70% of the cases. Obviously, at that time crude venoms were employed without even an adequate knowledge of the source. Sometimes the venoms from cobras captured in India or in South Africa were employed indistinctly. However, several reports mentioned besides the analgesic effect, an improvement in the condition of the patients.

Independently, the first cytotoxic component to be isolated and purified to homogeneity from a snake venom was a cytotoxin obtained by BRAGANCA et al. (1967) from Naja naja naja venom. TAKECHI et al. (1971) isolated two cytotoxins from the same venom having a high cytotoxic activity on tumor cells. COTTE et al. (COTTE, C. A.; ESSENFELD-YAHR, E. and CALVO LAIRET. A., 1972, Toxicon, 10, 157–163) showed the cytotoxic effects of Crotalus and Bothrops venoms on several cell lines. However, the high concentrations required (100 ug/ml) and the complexity in composition led to the conclusion that the cytotoxic action was a reflect of their non-specific toxic effects. On the other hand, recently, MARQUARDT et al. (MARQUARDT H., TODARO G. J. and TWARDZIK D. R., 1988, U.S. Pat. Nos. 4,731,439 and 4,774,318) demonstrated the high cytotoxic activity of polypeptides with low molecular weight (Growth Arresting Peptides, "GAP") isolated from the venom of Crotalus atrox.

The fraction called "crotoxin" from the Crotalus durissus terrificus venom was isolated by SLOTTA K. H. and FRAENKEL-CONRAT H. Since neither electrophoresis nor ultracentrifugation indicated gross lack of homogeneity, and in addition crotoxin was crystallizable, the fraction was regarded as an homogeneous chemical entity.

In 1971, two research groups (RUBSAMEN, K.; BREITHAUPT, H. and HABERMANN, E., 1971, Naunyn-Schmiedeberg,s Arch. Pharmac., 270, 274–288; HENDON, R. A. and FRAENKEL-CONRAT, H., 1971, Proc. Natl. Acad. Sci. U.S.A., 68, 1560-1563) reported almost simultaneously the separation of the unmodified components of the crotoxin complex. One is a basic phospholipase A2, having a molecular weight of 14500 and an isoelectric point 9.7, which is called crotoxin B, or subunit B (for basic). The other component is an acidic peptide of molecular weight 9500 and isoelectric point 3.5 which is devoid of enzymatic activity and is called crotoxin A, or subunit A (for acidic).

SUMMARY OF THE INVENTION

An object of this invention is a pharmaceutical composition useful for treatment of carcinomas, which comprises crotoxin complex (the complex of crotoxin A and crotoxin B in a molar ratio 1:1) from Crotalus durissus terrificus venom as therapeutic agent in a pharmacologically acceptable vehicle.

A further object of this invention is a method of treatment of carcinomas which comprises the administrating to patients therapeutically efficient amounts of a pharmaceutical composition including crotoxin complex in a pharmacologically acceptable vehicle.

These and other objects, advantages and novel aspects of the present invention will be made evident through the below detailed description of the invention.

DETAILED DESCRIPTION OF THE INVENTION

The present invention is based on the discovery by the applicants of certain properties of the reconstituted crotoxin complex (the 1:1 complex between subunits A and B), its pharmacodynamics and pharmacokinetics.

In our lab, we have separated the basic phospholipase $A_2$ (crotoxin B) and the acidic subunit (crotoxin A) from the native crotoxin complex by means of a procedure comprising:

(1) Separation of the crude crotoxin complex from Crotalus durissus terrificus venom by gel-filtration on Sephadex G-75 at pH 4.5.

(2) Separation of the subunits by ion-exchange chromatography on CM-Sephadex C-50 at pH 3.5 and elution with a concave gradient of buffer molarity from 0.1 to 1.0 M, followed by a linear gradient from 1.0 to 3.0 M of the buffer.

(3) Crotoxin A is further purified by ion exchange chromatography on DEAE-Sephadex A-50 at pH 6.5 and the basic phospholipase A2 (crotoxin B) is further purified by rechromatography on CM-Sephadex C-50 at pH 3.5.

The purified fractions behave as homogeneous materials by SDS-polyacrylamide gel electrophoresis and immunoelectrophoresis.

In the interest of clarity, when referring to subunits A and B, they correspond to crotoxin A (acidic peptide) and crotoxin B (basic phospholipase A2) separated (isolated) or in a 1:1 complex.

1. PROPERTIES OF THE SEPARATED SUBUNITS OF THE NATIVE CROTOXIN COMPLEX

1.A. Properties of crotoxin B

Crotoxin B is a phospholipase A2 which catalyzes the hydrolysis of the ester bond in position 2 of the glycerol moiety of the 1,2-diacyl (1-alkenyl-2-acyl- or 1-alkyl-2-acyl-) -sn-3-phosphoglycerides (phospholipids I), according to the following scheme:

$$\begin{array}{l} H_2C-O-CO-R_1 \\ | \\ R_2-CO-O-C-H \\ | \\ H_2C-O-PO^-_3-R_3 \end{array} \longrightarrow$$

I

-continued
$$\begin{array}{c} H_2C-O-CO-R_1 \\ | \\ HO-C-H \\ | \\ H_2C-O-PO^-_3-R_3 \end{array} + R_2-COOH$$

II           III where R1 and R2 are fatty acid residues and R3 may be: H (phosphatidic acid, PA), a polyalcohol (like glycerol in phosphatidylglycerol, PG, or inositol in phosphatidylinositol, PI) or a nitrogen-containing alcohol (like choline in phosphatidylcholine, PC, ethanolamine in phosphatidylethanolamine, PE, serine in phosphatidylserine, PS). The reaction products are a free fatty acid (III) and the 1-acylderivative (II) generally referred to as lysoderivative. The reaction is stereospecific and exhibits a specific requirement for Ca2+ ions as cofactor.

The basic phospholipase A2 (crotoxin B) hydrolyzes phospholipids in different states of aggregation, such as short-chain lecithins (obtained by chemical synthesis) as monomeric solution in water or aggregated as micelles as well as long-chain phospholipids (fatty acid chains C16 to C22) aggregated as vesicles, liposomes or in biologically important structures such as lipoproteins and membranes. Its specific activity on egg-yolk lipoproteins (pH 8.0, 30 C and Ca2+ 10 mM) is 200 umol of substrate hydrolyzed per minute and per mg protein.

The amino acid sequence of crotoxin B (AIRD, S. D.; KAISER, I. I.; LEWIS, R. V. and KRUGGEL, W. G., 1986, Arch. Biochem. Biophys., 249, 296-300) exhibits a high degree of homology with other phospholipases $A_2$. On the other hand, it shows an extremely high reactivity with p-bromophenacyl bromide (an active site-directed inhibitor of phospholipases $A_2$) with a pseudo-first order rate constant for inactivation which is 4 to 26-fold higher than that observed with other enzymes. It appears to have an hydrophobic area close to the active site at which it binds nitroxide-labeled fatty acids with an apparent Kd of 15 uM. This area is thought to be the region involved in the tight binding of the subunit B to phospholipid-water interfaces.

Gel-filtration experiments show that crotoxin B is able to interact with phospholipid aggregates, like mixed micelles of phospholipids: Triton X-100 or phospholipid : lysophosphatidyl choline (1:1), as well as with phospholipid vesicles either zwitterionic (like PC or 1:1 codispersions of PC:PE) or having negative charge (like PS, PA or PG). The specific activity of crotoxin B on different phospholipid vesicles appears to be similar, and is strongly affected by the physical state of the lipid.

Fluorescence spectroscopy studies of crotoxin B in the presence of phospholipid vesicles shows an increase of 100% in the emission intensity compared to that of crotoxin B alone and a blue-shift of the wavelength of maximal emission from 354 to 340 nm, reflecting the interaction with the phospholipid-water interface. The interaction is fast since maximum fluorescence intensity is reached in less than 5 min. The dependence of the change in fluorescence intensity with the phospholipid concentration indicate a strong preference for negatively charged phospholipids as indicated by the apparent dissociation constant which falls from 1-2 mM for PC or 1:1 codispersions of PC:PE to values <3 uM for 1:1 codispersions of PC:PS, PC:PA or PC:PG.

On the other hand, the binding of crotoxin B to negatively charged vesicles which contained entrapped 6-carboxyfluorescein, determined the release of the fluorophor which is 80% complete in about one minute. This indicates that the binding of crotoxin B to the vesicles results in perturbation and even disruption of the vesicular structure, as confirmed by electron microscopy of vesicle samples examined by negative staining. This effect is rapid and probably not related to the enzymatic activity of crotoxin B.

Concerning its biological activity, crotoxin B displays neurotoxicity resulting from the blockage of the neuromuscular transmission at the presynaptic level. For a review, see HABERMANN E. & BREITHAUPT H., 1978 Toxicon 16, p. 19-30.

In mice, by intravenous or intraperitoneal injection the $LD_{50}$ is about 0.6 ug/g of body weight. There exist a considerable difference in sensitivity among species. Compared to mice, chicks are 200 fold more sensitive, while rats are about 10 fold more resistant.

Relevant to the present invention, when added to cultures of normal or tumor cells, crotoxin B adsorbs in a non-saturable manner to cell membranes and displays cytotoxic activity towards hepatocytes, fibroblasts or Ehrlich ascites tumor cells. The cytotoxic and lytic action on cell membranes is strongly enhanced or potentiated by sublytic concentrations of the basic, non-neurotoxic proteins found in the venoms of snakes of the Gen. Naa, generically called cardiotoxins, cytotoxins or cobramines (an example of a cardiotoxin fraction is described herein under Section VII) as well as by the lytic peptides melittins (the fraction used was purchased from Sigma Chemical Co., St. Louis, Missouri).

1.B. Properties of crotoxin A

Crotoxin A is formed by three polypeptide chains A, B and C crosslinked by disulfide bonds, and the N-terminal amino acids of the B and C chains are blocked (BREITHAUPT, H.; RUBSAMEN, K. and HABERMANN, E., 1974, Eur. J. Biochem. 49, 333-345). Chains A and C have been sequenced as well as 24 of the 34 amino acid residues of chain B (AIRD, S. D.; KAISER, I. I.; LEWIS, R. V. and KRUGGER, W. G., 1985, Biochemistry 24, 7054-7058) and the sequence suggests that the subunit A derives from the structure of a phospholipase $A_2$ which have lost certain residues presumably implicated in the interaction with membranes.

It does not have any enzymatic activity and is not toxic to mice ($LD_{50} > 50$ µg/g body weight).

Gel-filtration experiments using $^{14}C$-crotoxin A and either mixed micelles of phospholipids with Triton X-100 or phospholipid vesicles showed that the A subunit does not interact with phospholipid-water interfaces regardless the phospholipid composition.

Crotoxin A displays four properties which are relevant in context with the basic C. d. terrificus phospholipase $A_2$ (crotoxin B) only:

(a) When combined with this phospholipase $A_2$ (crotoxin B) at molar ratio 1:1, it yields stable, non-covalent complexes (Kd $=10^{-10}$ M) with lower isoelectric point (4.3-4.5) and molecular weight of about 25000, thus restituting the physicochemical properties of the native crotoxin complex;

(b) It decreases the enzymatic activity of the basic phospholipase $A_2$, and (c) It increases the neurotoxicity of crotoxin B but not of phospholipases from other sources.

(d) It strongly decreases the interaction of crotoxin B with zwitterionic phospholipid-water interfaces as well as with the plasma membranes of the normal cells tested, as herein mentioned, but seems to be less effective in inhibiting the interaction of crotoxin B with the membranes of the tumor cell described below.

2. PROPERTIES OF THE CROTOXIN COMPLEX

The 1:1 complex between crotoxin A and crotoxin B is quite stable at neutral pH, but can be dissociated into the free subunits at pH values below 3.0.

The complex is more neurotoxic to mice than the isolated crotoxin B ($LD_{50}=0.12$ ug/g body weight when administered intravenously or intraperitoneally and 0.5 ug/g body weight when administered subcutaneously). Crotoxin A potentiates the neurotoxicity of the basic phospholipase $A_2$ (crotoxin B) by preventing its unspecific binding to membranes, thus allowing the subunit B to reach the neuromuscular junction where the complex dissociates: the subunit B binds to the membrane and the subunit A is released to the medium (cf. JENG T. W.; HENDON R. A. and FRAENKEL-CONRAT H., 1978, Proc. Natl. Acad. Sci U.S.A. 75, 600–604; HABERMANN E. and BREITHAUPT H., 1978, Toxicon 16, 19–30).

In the crotoxin complex, the basic phospholipase $A_2$ (crotoxin B) does not react with p-bromophenacyl bromide nor is able to bind nitroxide-labeled fatty acids, indicating that crotoxin A reduces the accessibility of an hydrophobic area on the surface of crotoxin B, but does not occlude the active site of the enzyme to short-chain lecithins.

The phospholipase $A_2$ activity of the complex is 10% to 50% of that of isolated crotoxin B depending on the substrate. When measured on PC vesicles it is about 10% of that of crotoxin B and is not affected by changes in the physical state of the phospholipid. Gel-filtration experiments with mixed micelles of PC:LysoPC, PC:Triton X-100 or with vesicles of PC or codispersions 1:1 PE:PC (i.e., zwitterionic phospholipids) shows that, differently from crotoxin B, the crotoxin complex is unable to interact with the zwitterionic phospholipid-water interfaces. Therefore, the decrease in phospholipase $A_2$ activity of crotoxin B in the complex mainly reflects its inability to bind to aggregated phospholipid.

This seems to be also the case with biological membranes. The binding of crotoxin B to erythrocytes or electroplaques is non-specific and non-saturable (JENG T. W.; HENDON R. A. and FRAENKEL-CONRAT H., 1978, Proc. Natl. Acad. Sci. U.S.A., 75, 600–604; BON C.; CHANGEUX J. P.; JENG T. W. and FRAENKEL-CONRAT H., 1979, Eur. J. Biochem. 99, 471–481) and is strongly reduced in the complex with crotoxin A. This inhibition of the unspecific binding of crotoxin B by complex formation with crotoxin A abolishes some pharmacological actions of isolated crotoxin B, like the induction of blood platelet aggregation, or inhibition of blood coagulation.

On the other hand, gel-filtration experiments in the presence of mixed micelles or vesicles of strongly acidic phospholipids (PS, PA, PG or PI) show that these strong negatively charged surfaces are able to dissociate the crotoxin complex. The subunit B remains bound to the aggregated phospholipid, while the radiolabeled subunit A remains soluble. Measurements of fluorescence intensity with the crotoxin complex in the presence of negatively charged phospholipid vesicles show that fluorescence intensity increases much more slowly than with isolated component B (the half-effect occurs in about 20 min and the maximal value is reached in about 2 hr), indicating that the slow dissociation of the crotoxin complex in the presence of negatively charged phospholipid vesicles is the rate limiting step in the binding of crotoxin B.

JENG et al.(JENG, T. W.; HENDON, R. A. and FRAENKELCONRAT, H., 1978, Proc. Natl. Acad. Sci. U.S.A., 75, 600–604) using doubly labeled crotoxin complex have shown that crotoxin A which does not bind to membranes inhibits the binding of crotoxin B to erythrocytes. However, if erythrocyte ghosts are employed, the subunit B binds to the membrane and the subunit A is released to the supernatant, which can be explained as the result of the accumulation of acidic phospholipids on the inner leaflet of the red cell membrane becomes accessible and dissociates the crotoxin complex.

These results indicate that binding of the basic phospholipase $A_2$ (crotoxin B) to model systems (micelles or vesicles) or to biological membranes require the dissociation of the complex with crotoxin A. Furthermore, once crotoxin B is bound to any phospholipid-water interface, the addition of crotoxin A cannot displace the enzyme to reform the crotoxin complex.

3. PHARMACODYNAMICS

Any effect of the crotoxin complex on an aggregated phospholipid or a biological membrane obviously requires (1) the interaction of subunit B with the surface and (2) the enzymatic hydrolysis of phospholipids catalyzed b crotoxin B.

We have demonstrated that the active site of crotoxin B in the complex is accessible to synthetic, water-soluble substrates and that its catalytic function seems to be maintained. Therefore, the inhibition of the phospholipase A2 activity of crotoxin B in the complex is due to the fact that crotoxin A prevents the binding of the basic phospholipase A2 (crotoxin B) with zwitterionic (or having a weak negative charge, 5% of acidic phospholipid and 95% of zwitterionic PC) phospholipid-water interfaces. Conversely, the interaction of crotoxin B with surfaces having a strong net negative charge is not affected by crotoxin A since these surfaces induce complex dissociation. Thus, the binding of crotoxin B to phospholipid-water interfaces occurs only with (or after) complex dissociation.

We have found that if the crotoxin subunits are covalently crosslinked by a bifunctional reagent (dimethyl-suberimidate), the resulting "covalent" crotoxin complex loses completely its capacity to interact with aggregated phospholipids, while its phospholipase $A_2$ activity towards monomeric, short-chain substrates is preserved.

Using radiolabeled crotoxin complex ($^{125}$I-crotoxin B and $^{14}$C-crotoxin A), it can be shown that only crotoxin B binds to interfaces. In no case crotoxin A was shown to interact with interfaces or membranes.

Concerning the cytotoxic effects of crotoxin complex on Ehrlich ascites tumor cells, it was verified that a concentration of about $9 \times 10^{-7}$ M led to lysis of the cultured cells, starting at 60 min incubation and being 80% complete in 24 hr. On the other hand, about 10% to 15% of hepatocytes or fibroblasts were dead after similar treatment.

The effect could be reproduced with 3.45 ug/ml of isolated crotoxin B, except that 45–60% of the fibroblasts appeared dead at the end of the experiment. Crotoxin A had no effect on either tumor or normal cell cultures even at 20 ug/ml.

Concerning the possible mechanism of action, the following observations are important:

(a) Crotoxin B appears to be the component of the crotoxin complex responsible for the cytotoxic effects on tumor as well as in normal cells. In both cases, the addition of crotoxin B produced evidence of cellular damage and no effect was observed after the addition of isolated crotoxin A.

(b) The cytotoxic action of crotoxin B may be related to its phospholipase $A_2$ activity, since selective chemical modification with p-bromophenacyl bromide (an active site-directed inhibitor of phospholipases $A_2$, cf. VOLWERK, J. J.; PIETERSON, W. A. and DE HAAS, G. H., 1974, Biochemistry 13, 1446-1454) decreases (but not abolishes) the cytotoxic activity. In model systems (phospholipid vesicles) the addition of chemically modified crotoxin B resulted in an increase in the fluorescence intensity of about 85% of that exhibited by native crotoxin B, indicating that the modified crotoxin B binds to the vesicle. Furthermore, the binding of modified crotoxin B also results in perturbation of the vesicle structure as shown by the leak of entrapped 6-carboxyfluorescein. These effects on the stability of the phospholipid vesicles occur within one minute after the addition of either native or modified crotoxin B and are therefore independent of the enzymatic activity.

(c) Applicants' investigations show that crotoxin complex appears to exhibit a more intense cytotoxic action on the tumor cells than in normal cells, as mentioned above.

(d) There exist abundant evidence that tumoral transformation results in pleiomorphic changes and alteration of numerous membrane functions. Alterations in adhesiveness and the absence of growth inhibition by contact; the absence of contact inhibition and a greater fusogenic capacity, seemingly run parallel with malignity; and changes in the surface potential, alteration in permeability and immunological changes have been reported. The appearance of new or embryonic antigens, as well as the deletion of certain specific antigens have been observed in several spontaneous or experimental tumors. For a review see WALLACH D. F. H.

(e) Regardless of whether the interaction with crotoxin B occurs due to the previous dissociation of the crotoxin complex in the vicinity of the membrane, or to the presence on the membrane of "high affinity sites" capable of competing with the subunit A of the complex, the net result must be the binding of crotoxin B to the membrane and the subsequent hydrolysis of membrane phospholipids. The hydrolysis products of the phospholipase $A_2$ activity are fatty acids and lysoderivatives which are able to alter the permeability properties and, at higher concentrations, to affect the stability of the lamellar structure. In model systems like phospholipid vesicles, the addition of 1-3 moles of lysoderivatives per 100 moles of phospholipid determines the increase in permeability to entrapped solutes like sucrose or cations and at higher ratios may disrupt the lamellar structure.

Conclusions

Crotoxin B produces cytotoxic effects on normal and tumor cells upon interaction with the cell membrane as a result of the structural perturbation induced by the binding itself as well as due to the local increase in concentration of products of the phospholipid hydrolysis. It is not known at present whether internalization of the enzyme is also required to produce cytotoxic effects.

In the crotoxin complex, the subunit A may function as a pharmacokinetic carrier molecule for the basic phospholipase $A_2$ (crotoxin B). The acidic subunit A, having a high affinity for the basic phospholipase $A_2$ may prevent the non specific adsorption of crotoxin B to many acidic tissue constituents, thus preserving it for "specific" or "high affinity sites" which may display an affinity for crotoxin B still higher than that of crotoxin A.

Near or at these "high affinity sites", either there exist a set of physicochemical conditions which promote dissociation of the crotoxin complex and the subsequent binding of crotoxin B to the membrane, or transient ternary complexes (crotoxin A-crotoxin B-"site") are formed which eventually leads to stabilization of the crotoxin B-"site" complex and the release of crotoxin A. The binding of crotoxin B to membranes and to crotoxin A appears to be mutually exclusive phenomena.

Some tumor cells are more sensitive to the cytotoxic action of the crotoxin complex. Thus, several possibilities must be taken into account, namely (a) the membrane of these tumor cells may contain a larger set of structural elements able to function as "high affinity sites" for crotoxin B;

(b) these cells may establish in its neighborhood a set of physicochemical conditions which promote complex dissociation and subsequent binding of the crotoxin B to the membrane;

(c) in addition, these tumor cells may have a reduced capacity to compensate for the structural perturbation of the membrane produced by the binding of the enzyme and the increase in the local concentration of products of the phospholipid hydrolysis.

4. PHARMACOKINETICS

Pharmacokinetic studies were carried out using basic phospholipase $A_2$ (crotoxin B) labeled with $^{125}I$ and, in some cases with the doubly labeled complex with $^{14}C$-crotoxin A obtained by reaction with $^{14}C$-acetic anhydride.

4.1. Distribution

Two groups of host animals were sacrificed 30 and 60 min after the intravenous injection of 220 ug of crotoxin complex ($^{125}I$-crotoxin B) and the concentration in different organs was determined (fmoles = $10^{-15}$ moles).

| Tissue or organ | Time post-injection | |
|---|---|---|
| | 30 min | 60 min |
| Spleen | 17500 | 2600 |
| Brain and spinal chord | ND | ND |
| Heart | 3210 | 118 |
| Stomach | 216 | ND |
| Liver | 2208000 | 1560200 |
| Small intestine | 366 | ND |
| Large intestine | 154 | ND |
| Skeletal muscle | 178000 | 71000 |
| Urine | 354000 | 2000 |
| Lungs | 68000 | 780 |
| Kidneys | 710000 | 266200 |
| Bladder | ND | ND |
| Percentage of total | 84.5 | 45.4 |

Note: The injected animals exhibited serious respiratory insufficiency and were maintained with artificial respiration until sacrificed.
ND = non detectable above the background.

The basic phospholipase $A_2$ is concentrated in the liver wherein it is degraded passing to the amino acid pool. The hematoencephalic barrier is impermeable to crotoxin and it does not appear in significant amounts in central nervous system organs. Appearance in urine may be due to the high doses employed.

4.2. Biotransformation, excretion and final metabolites The biotransformation products are amino acids which follow their respective metabolic pathways. Consequently there are no specific excretion metabolites.

5. STUDIES ON CELL CULTURES

The cytotoxic action of the crotoxin complex was tested with the human tumor cell lines Hs 57 8T (ATCC HTB 126) a breast carcinoma, SK-LU-1 (ATCC HTB 57) a lung adenocarcinoma and U-87 MG (ATCC HTB 14) a glioblastoma.

The cells were plated in 24 well culture dishes using about $5 \times 10^4$ cells per well in 1.0 ml of a 1:1 mixture of Dulbecco Modified Eagle's Medium (DMEM) and Ham's nutrient medium F 12 (DMEM:F 12) supplemented with 10% fetal bovine serum (FBS) and cultured at 37 C and more than 90% humidity in 5% C02 in air. The appearance of the culture was routinely monitored using phase-contrast microscope.

One day after plating the cells crotoxin was dissolved in DMEM:F 12 with 10% FBS and aliquots were added to the cultures to make a total volume of 2.0 ml per well.

Cells were observed microscopically after one and three days of treatment.

In order to determine the number of cells remaining attached in the cultures after three days incubation the medium was aspirated, the wells rinsed with an isotonic saline solution and the cells were detached with trypsin-EDTA (0.5 ml per well). The trypsin was neutralized with 0.5 ml DMEM:F 12 with 10% FBS and the entire content of each well was added to 9.0 ml of isotonic saline solution and counted in a Coulter counter.

All the tumor cell lines were sensitive to the cytotoxic action of crotoxin. With the cell lines SK-LU-1 and Hs 57 8T the apparent value of the $IC_{50}$ was about 4 ug/ml, while wells treated with concentrations of crotoxin of 9.5 ug/ml or higher contained primarily cell debris at the end of the experiment. Many of the cells treated with intermediate concentrations of crotoxin appeared dead, thus the cytotoxicity was probably greater than is evident based on the relative cell number. The U-87 MG cells required higher crotoxin concentrations, with an apparent $IC_{50}$ value of 9.5 ug/ml and the cells treated with a concentration of crotoxin of 16.9 ug/ml or higher appeared dead.

Conversely, a culture of normal human keratinocytes is less sensitive to the cytotoxic action of crotoxin. The cultures (NHEK-47) maintained in serum-free KGM T medium (keratinocyte growth medium from Clonetics Corporation, San Diego, CA) did not show substantial difference in the number of cells after treatment with crotoxin concentrations of 2.3 to 12.7 ug/ml. The apparent decay may not be significant given the variability of the untreated cell cultures. In addition, toxic effects from the treatment with lowest concentrations were not apparent under the microscope. However, both microscopic examination and cell counting indicated that fewer cells were present after treatment with crotoxin concentrations from 17 to 30 ug/ml, with an apparent $IC_{50}$ value of 20-30 ug/ml.

Therefore, crotoxin is toxic to those human tumor cells at relatively low concentrations (2 to 12 ug/ml) and it appears to be more toxic to tumor cells than to normal human epidermal keratinocytes. A single concentration of crotoxin of 13 ug/ml kill all the cells in cultures of SK-LU-1 and Hs 578T cells, 85% of the cells in cultures of U-87 MG cells and only 11-16% of the cells in a culture of normal human keratinocytes.

6. ANIMAL STUDIES

In accordance with the conventional protocol of the National Cancer Institute (N.C.I.-U.S.A.) the tumors melanoma B 16, colon tumor 26 and Ridgway's osteogenic sarcoma were used to evaluate the antitumoral activity of the crotoxin complex. These studies presented the problem of the extremely high sensitivity of mice to the intrinsic neurotoxicity of the cortoxin complex (see points 1.A and 1.C). Therefore, in this case an increase in the average survival time exceeding 20% and/or inhibition of local growth greater than 50% are required to demonstrate antitumor activity in comparison with non-treated controls.

Mice were injected subcutaneously with 30-40 ng/g of body weight every four days after the inoculation of the tumor and the treatment was continued for 90 days.

With melanoma B 16 there was an increase in the average survival time of 50-200% with 55-80% survivors after 90 days.

With colon tumor 26, there was an increase in the average survival time of 80-100% with 60-80% of survivors after 90 days.

With Ridgway's ostengenic sarcoma, there was an increase in the average survival time of 70-100%.

The high mortality (20-45% of the animals) is a consequence of the high neurotoxicity of crotoxin on mice. However, this high sensitivity is characteristic of the species and not a general phenomenon. In fact, rats can tolerate easily 100 ng/g of body weight intravenously and as much as 600 ng/g subcutaneously.

Smaller doses of crotoxin (<10 ng/g of body weight) or the intraperitoneal administration of 10-20 ng/g body weigh each 10th and 11th days (e.g. at days 10 and 11, 20 and 21, etc.) did not result in a significant increase in the average survival time (10-20%).

CLINICAL RESULTS

The following case histories are representative of a group of patients with advanced stages of cancer which demonstrates the clinical efficacy of the present compound.

EXAMPLE 1

Female, 51 years old who on Apr. 1, 1986 was submitted to mastectomy for a tumor in her left mammary gland. The pathology report was: infiltrating ductal carcinoma with nine lymphatic nodes showing metastasis. From April to August 1986 she was treated with chemotherapy (Endoxan, 5-FU, Methrotexate) and Tamoxiphen. The hepatic scintillation graph (Sep. 3, 1986) shows a high increase in size mainly at the expense of the left lobe with a zone of decreased uptake of the radioisotope having irregular limits, and several zones with similar characteristics in the right lobe. A bone scintillation graph (Sep. 20, 1986) showed several focus of increased uptake of the radioisotope at the upper third of the right humerus, lumbar vertebrae L IV and L V, right iliac crest and major trachanter of the right femur.

She started the parenteral treatment with crotoxin in November of 1986 and continued until February of 1987.

Two weeks after starting treatment the pains diminished and the patient was able to resume her usual activities. A bone scintillation graph (Jan. 5, 1987) was reported normal. A hepatic scintillation graph (Jan. 9, 1987) showed a diffuse hepatomegalia with a zone of decreased uptake of the radioisotope in the right lobe only. Mammography of the remaining mammary gland (Feb. 27, 1987) showed a slight dystrophia. The patient continued her active life without additional treatments and returned periodically for control. Bone scintillation graphs (Jun. 7, 1988; May 3, 1989) are normal. Hepatic scintillation graphs (Jul. 7, 1988; May 15, 1989) showed the organ uniformly enlarged but with a uniform distribution of the radioisotope.

EXAMPLE 2

Female, 64 years old with an abdominal tumor mass which, according to CAT scan (February 1985) was 8 cm diameter having irregular borders, comprising the cephalo-isthmic portion of the pancreas, displacing forward and outward the antrum-pylorus-duodenal region with loss of perivisceral and perivascular limits. In addition, there were isolated retroperitoneal nodular images. An ecographic study (August 1985) reported a pancreatic tumor ($8 \times 10$ cm) comprising isthmus and body, having irregular borders and displacing the big vessels. An exploratory laparotomy (Nov. 22, 1985) showed a tumor comprising pancreas fixed to the retroperitoneum and to big vessels, infiltrating the mesocolon and with multiple lymphoadenopathies at the root of the mesenterium. The tumor was not excised, but a sample was taken for pathology study which reported: desmoplastic indifferentiated carcinoma of probable pancreas origin. No satisfactory response was obtained after irradiation (4000 Rads, from January to February 1986) with linear accelerator and the patient was informed that there were no therapeutic possibilities with conventional treatments.

She started the parenteral treatment with crotoxin in May 1986 and continued until August 1986.

She resumed her active life a month after starting the treatment, was in good general condition and returned periodically for control. A new CAT scan (Nov. 17, 1987) showed only an area of low density at the cephalic portion of the pancreas, contacting the posterior wall of the stomach antrum without defined limits, but without comprising the rest of the pancreas. No displacement of the big vessels is observed. The patient continued her active life without any additional treatment.

EXAMPLE 3

Female, 58 years old, who had been submitted to enucleation of her left eyeball (Dec. 5, 1982) for an adenocaranone of the lacrimal sac. A CAT scan (May, 1984) showed a relapse of the tumor on the floor of the left orbit and was irradiated (6000 Rads from May 15 to Jul. 3, 1984). From November of 1984 to March of 1985 she received chemotherapy (5-FU, Doxorubicine and Cyclophosphamide), with an additional cycle of chemotherapy on May 1985 and no other treatment since then. On April of 1986 she presented a $5.5 \times 3.5$ cm lesion at the intercilliary region, which was hard and adhered to superficial and deep planes, accompanied with metastasis in the lymphatic nodes: on the right side there were a $2 \times 3$ cm submaxillary and a $3.5 \times 3$ cm preauricular, and on the left side there were a $2 \times 2$ cm submaxillary and several other with smaller size in the pre and post auricular region.

She started the parenteral treatment with crotoxin in May of 1986 and continued until January of 1987; followed by the intralesional injection of 0.3 mg of crotoxin each ten days until April 1987.

On September of 1986 the main lesion was $4 \times 3$ cm; it disappeared progressively and on April 1987 it remitted completely. The lymphoadenopathies were reduced in size and number and three of them disappeared completely. This allowed the patient to resume her social life which she abandoned esthetic reasons. The patient did not receive any additional treatment until October of 1988, when there was a relapse of the tumor but at the lymphatic nodes only, and since she refused to be treated with chemotherapy, the lymphatic nodes were irradiated with excellent results as shown in two successive CAT scan (Oct. 18, 1988 and Jun. 2, 1989). A new lymphatic metastasis appeared on July, 1989 which was irradiated. A bone scintillation graph (August of 1989) showed some increased uptake of the radioisotope at the left orbit, but it is not clear whether it is due to a relapse of the tumor, and is now under study. The patient is in good general condition and continues her active life.

EXAMPLE 4

Female, 35 years old, was in bed with pain and her right leg flexed and unable to walk due to a $13 \times 10 \times 8$ cm tumor in her lower pelvis which took internal and external obturator muscles and was limited at the back by the right gluteus maximus. Pathology report was: liposarcona with round cells. On Jun. 23, 1986 was treated with two series (15 days apart) of 180 mg of cysplatinum. On Sep. 9, 1986, a CAT scan showed a 70% increase in the tumor size, which have grown into the pelvis and displaced the bladder.

The patient started the parenteral treatment with crotoxin in September of 1986 and continued until November of 1986.

One month after starting the treatment there was a 30% reduction of the tumor size, pain disappeared and the patient was able to walk. During the next month the tumor became softer and had a further 20% reduction in size. The patient was able to walk almost normally and gained some weight. Three months after the suspension of the treatment the patient died of an intercurrent infection which could not be controlled.

EXAMPLE 5

Male, 45 years old, was submitted to a laparotomy on Feb. 1, 1986 and the diagnostic is pancreas adenocarcinona with invasion of the retroperitoneum. The tumor was not removed. No treatment was performed and he received analgesics only. The patient lost 20 Kg weight within three months and remained in bed with pain.

He started the parenteral treatment with crotoxin in April of 1986 and continued until July of 1986.

Fifteen (15) days after starting the treatment the pain diminished, the consumption of analgesics was reduced and the patient walked without difficulties. Since he scarcely had any abdominal pain he resumed his work as specialist on maxillary-facial surgery and, at the end of May 1986 he abandoned the whole analgesic treatment. An ecographic study (September 1986) reported: pancreas head of normal size and increased ecogenicity, with regular borders of 18 mm diameter; pancreas body presented a hyecogenic mass of 23×26×30 mm; retroperitoneum free. Further studies of CAT scan and selective arteriography of celiac trunk showed that the tumor mass had a 65% reduction in size and the retroperitoneal infiltration disappeared. However he had some abdominal disorders and consulted a gastroenterologist who suggested him to perform a gastroduodenopancreatectomy with splachnic blocking. In spite of the opinion of several doctors, surgery was performed on September 20 and four days later the patient died due to postsurgery complications.

EXAMPLE 6

Male, 40 years old who presented important ascitis and was submitted to abdominal puncture (Feb. 14, 1986) whereby 2000 ml of liquid were removed. Cytologic examination reported: peritoneal mesotheliona. An exploratory laparotomy was performed on February 15, 1986, which showed multiple metastasis on major epiploom, parietal and visceral peritoneum. The pathology report was: mesotheliona of papillar type. The oncologists decided against chemotherapy in view of the patients poor general condition (he had lost 18 Kg) and the advanced state of the disease, and applied only palliative treatment with Tegafur R and Deltisone R.

Parenteral treatment with crotoxin was started in April of 1986 and continued until June of 1986.

Thirty days after starting the treatment the ascitis was significantly reduced and abdominal punctures were no longer required. During May of 1986 the ascitis disappeared and the patient increased in weight from 58 to 70 Kg (his normal weight was 76 Kg) and resumed his normal life. He continued improving during June of 1986 and even practised sports tennis). At the end of July, the patient is in good general condition but ascitis reappeared. An abdominal puncture (Sep. 1, 1986) removed 1800 ml of liquid; however, cytologic examination did not find tumor cells. The oncologists decided then for chemotherapy so that patient received cysplatinum (Oct. 23, 1986). Immediately after there appeared incoercible bilious vomits, dehydration and loss of weight. In spite of these symptoms a second series of cysplatinum was applied on Nov. 18, 1986. A new exploratory laparotomy was performed (Feb. 3, 1987). The pathology report indicated the absence of malignant tissue. The patient remained in hospital without specific treatment and died on Mar. 19, 1987.

EXAMPLE 7

Female, 39 years old, was submitted to laparotomy (Oct. 24, 1985) for a 12×6 cm tumor occupying the subperitoneal pelvis space, tightly adhered to the anus deviation, to vagina, bladder and to the back portion of osteomuscular planes. Since it was impossible to remove the tumor, a biopsy was taken and the pathology report was: indifferentiated fusocellular sarcona. A CAT scan (Dec. 3, 1985) indicated a solid tumor with unclear borders which occupied retrovesical and pararectal spaces; the post lateral wall of the bladder was compressed by the tumor mass. The patient was irradiated (7000 Rads, from Dec. 3, 1985 to Feb. 10, 1986). But a new CAT scan (Mar. 3, 1986) showed that the tumor had progressed forward to the right frontlateral wall of the bladder; upwards there appeared multiple solid retrovesical nodular formations; the retroperitoneal space occupied by indefinite solid images compatible with lymphoadenopathies. The patient had edema of the right leg with noticeable superficial venous circulation, reduction of temperature and cyanosis of the right foot and pain in the internal region of the muscle.

Parenteral treatment with crotoxin started in May 1986 and continued until July 1986.

Twenty days (20) after starting the treatment, the pain in her right leg disappeared and the edema was significantly reduced. During June of 1986 the edema disappeared completely, the patient put on weight, felt good and resumed her work. A CAT scan (Jul. 24, 1986) showed that the tumoral mass disappeared, remaining only an increased thickness at the right postlateral wall of the bladder, which could be a post surgical effect. No other treatment was applied. The patient is presently in a good clinical condition, works actively, her weight is 50 Kg (her usual weight was 48 Kg) and returns periodically for control.

EXAMPLE 8

Male, 5 years old, who had permanent cephalea, could not stand on his feet, had difficulties when coughing and swallowing and presented a right convergent strabismus. A CAT scan (Apr. 11, 1986) reported hydrocephalia but no pathologic images in cerebral trunk or cerebellum. A ventricle-peritoneal derivation valve was installed (May, 1986) and he remained in hospital. On Jun. 1, 1986, a brain arteriography showed a stop at the brain trunk and a new CAT scan (Jun. 4, 1986) indicated a tumor of the cerebral trunk (presumably a glioma) with noticeable supratentorial obstructive hydrocephalia. Without pathologic confirmation the patient was irradiated (5000 Rads from Jun. 10 to Jun. 30, 1986) and his general condition showed some improvement. Two successive CAT scan studies (July 30 and Aug. 8, 1986) reported a round hypodense lesion in the pontobulbar region, particularly on the right, side which occupied almost the whole pontine segment. The fourth ventricle was deformed on the middle line and displaced downwards; peri trunk cisternae were collapsed and the subarachnoid spaces at the convexity were not visualized. The diagnosis was expansive lesion of the pontobulbar region with slight mass effect. On Sep. 15, 1986, the patient was operated and a biopsy was taken; the pathology report was: mixed glioma (grade III) with predominant astrocytic component. The patient remained with quadriplegy, dysfagia, difficult breathing, fever, sphincter incontinence, convergent strabismus of the right eye and palpebral ptosis. His weight was 16 Kg and received food by naso gastric catheter. On Oct. 20, 1986, a new CAT scan showed a large lesion with low, heterogeneus density occupying the pontine mesencephalic zone with a moderate mass effect and perilesional edema; lateral ventricles expanded and asymmetric; the third ventricle was broadened at the middle line and the fourth ventricle was collapsed and deformed. The basal cisternae were collapsed and Silvian cistern and subarachnoidal spaces at the convexity were not visualized.

Parenteral treatment with crotoxin was started in November of 1986 and continued until March of 1987.

The patient gradually recovered and, after 45 days of treatment his general condition improved. The fever, dysphagia, respiratory difficulties and palpebral ptosis dissapeared. The convergent strabismus of the right eye decreased considerably. He moved all his limbs, put on weight (5 Kg), was able to walk and speak. A new CAT scan (Dec. 13, 1986) showed the lesion of the bulboprotuberantial cap significantly reduced in size during the period of study; and hydrocephalia controlled by ventricular drainage. The patient returned home and resumed his familiar and social life. He put on weight, increased his height and during January of 1987 played with his friends, took baths at the swimming pool and rode bicycle. On Feb. 9, 1987, a CAT scan showed: hydrocephalia controlled by ventricular drainage. Deformation of the floor of the fourth ventricle at protuberantial level without conclusive tomographic evidences of residual tumor. After suspension of the treatment, he slowly returned to the condition he was in June 1986. The patient was in regular general condition but having quadriplegy, dysphagia, respiratory difficulties and long, intermittent periods with fever. A CAT scan performed on late April 1987 reported 70% tumor relapse.

EXAMPLE 9

Female, 40 years old, who was submitted to mastectomy on July of 1977 for an infiltrating ductal carcinoma in her left mammary gland and received 5000 Rads from July to December of 1977. In 1980 a control mammography reported a pathologic image in her right nipple. A mastectomy with removal of the axillary lymphatic nodes was performed and the pathology report was: infiltrating ductal carcinoma with two lymphatic nodes showing metastasis. She received chemotherapy (eleven cycles of CMF, June to September of 1980) and returned for control each two months. In February of 1986 a hard, painful protuberance in scalp was discovered. On Mar. 14, 1986, a CAT scan showed metastasis in calotte and lumbar vertebra L II; which was coincident with the result of a bone scintillation graph performed that same week. A calotte biopsy was obtained and the pathology report was: infiltration of bone and connective tissue by a poorly differentiated adenocarcinoma. Clinical examination at that time showed a 4×4 cm frontoparietal tumor, hard and painful.

Parenteral treatment with crotoxin started in April of 1986 and continued until July of 1986.

After forty five (45) days of treatment, there appeared a complete remission of the frontoparietal lesion and the patient resumed her usual activities. X-ray studies (Aug. 5, 1986) were reported normal and a CAT scan (Aug. 22, 1986) reported no lesion progress in calotte and recalcification of the lesion in L II. In October of 1986, a CAT scan showed the absence of lytic lesion in the spine and stabilization of the lytic lesion in calotte. In March of 1987 a CAT scan reported recalcification of the bone lesions and a bone scintillation graph was reported normal.

8. EXAMPLE OF PURIFICATION PROCEDURE a) Obtainment of the crude complex 500 mg of lyophilized material are suspended in 5 ml of 0.2 M sodium chloride solution, bi-sodium ethylenediamine tetraacetate lmM, and a buffer of ammonium formate 20 mM pH 4.0. The solution is centrifuged at 10,000 g for 20 minutes in a refrigerated Sorvall RC 2-B centrifuge at 4° C. and the yellowish and slightly turbid supernatant was aspirated with a plastic syringe coupled to a Teflon tube constitutes the starting material.

The remainder of the procedure is carried out in a cold chamber at 2-4° C.

Step 1: The starting material is dispersed in a Sephadex G-75 column (Pharmacia Ltd. Uppsala, Sweden) measuring 85×2.5 cm (417 ml) adapted for ascending flow and pre-balanced with ammonium formate buffer 0.1 M, pH 4.5 containing bi-sodium ethylendiamine tetraacetate 0.1 mM. The elution is carried out with the same buffer solution, recovering fractions of 3.0×3.2 ml at a flow velocity of 0.8×1.0 ml. cm$^2$.hour$^{-1}$. The crude complex is eluted in a value of Kav ($K_{av}=(V_e\cdot V_o)/(V_o-V_t)$) of between 0.40 to 0.50, and in particular, 0.44.

Fractions containing the crude complex are combined and concentrated by (a) lyophilization and (b) freezing, as upon defreezing the complex precipitates into an insoluble form and can be resuspended by homogenization in a Potter-Ehlvejen homogenizer having a Teflon pestle, or by ultrafiltration under nitrogen pressure in a chamber provided with a Diaflo UM-10 membrane (Amicon Co., Bloomington, Ma. USA) to a final volume of about 10 ml.

b) Separation of sub-units A and B from the crude complex

Step 2: The sample obtained in Step 1 is adjusted to a pH of 3.5 with acetic acid and is dispersed in a CM-Sephadex C-50 column (Pharmacia Ltd., Uppsala, Sweden) having 8×2 cm and pre-balanced with a buffer solution of ammonium formate 0.1 M, pH 3.5. Elution is commenced with a buffer solution of ammonium formate 0.1 M, pH 3.5 (250 ml) to elute sub-unit A which, under these conditions, is not retained by the exchanger. The elution is continued with a concave molarity gradient of the eluant (350 ml of ammonium formate 1.0 M, pH 3.5) (i.e., there is concave gradient of buffer molarity from about 0.1 M to about 1.0 M) and finally with a linear molarity gradient (110 ml of ammonium formate 1.0 M, pH 3.5 and 110 ml of ammonium formate 3.0 M, pH 3.5), (i.e., a linear buffer molarity gradient of from about 1.0 M to about 3.0 M) recovering 5 ml fractions at a flow velocity of 34 ml. cm$^2$.hour$^{-1}$. The elution diagram is followed, measuring adsorbency at 280 nm of eluted fractions. The last peak of protein eluted under said conditions corresponds to sub-unit B.

c) Purification of Sub-units

Step 3: Purification of sub-unit A

The fraction first eluted in Step 2 contains sub-unit A. The fractions are combined and dialyzed against 1000 ml (×3 times) of potassium phosphate (10 mM, pH 6.9) buffer solution. Alternatively, the combined fractions are concentrated by ultrafiltration under nitrogen pressure on a Diaflo UM-05 (Amicon Co., Bloomington, Ma. USA) and balanced with potassium phosphate (10 mM, pH 6.9) buffer by chromatography on Sephadex G-25 (Pharmacia Ltd., Uppsala, Sweden).

The sample is applied on a DEAE-Sephadex A-50 column (10×1.5 cm) pre-balanced with potassium phosphate (10 mM, pH 6.9) buffer. Sub-unit A is eluted by means of a linear molarity gradient (100 ml of potassium phosphate 10 mM, pH 6.9+100 ml sodium phosphate 0.1 mM, pH 6.9).

Fractions containing purified sub-unit A are extensively dialyzed against 100 ml (×3 times) of 0.15 M NaCl and concentrated by ultrafiltration as previously mentioned.

The recovery of sub-unit A is of 37.5 mg of protein. Obtained under the above conditions, sub-unit A exhibits only one precipitation arc by immunoelectrophoresis over agar gel.

Step 4: Purification of Sub-Unit B

Fractions containing sub-unit B (eluted in last place in Step 2) are combined and the sample is lyophilized or dialyzed against 1000 ml (×2 times) of an ammonium formate buffer (0.1 M, pH 3.5) and chromatographed again on a CM-Sephadex C-50 column prebalanced with ammonium formate buffer (0.1 M, pH 3.5) as described in Step 2 with the exception that, once concluded the concave molarity gradient of ammonium formate up to 0.1 M, the elution is directly continued with ammonium formulate buffer (0.2 M, pH 3.5) so as to concentrate the active fraction.

The fractions containing purified and concentrated sub-unit B are extensively dialyzed against 1000 ml (×6 times) of 0.15 M NaCl.

The recovery of sub-unit B is of 75 mg of protein. Obtained under the above conditions and submitted to electrophoresis over polyacrylamide gel with sodium dodecylsulphate, it presents two strips with mobilities corresponding to molecular weights of 10,000 (monomer) and 20,000 (dimer).

Sterilization of purified sub-units

The preparations of sub-units A and B purified in a NaCl solution (0.15 M) are sterilized by filtration through Millipore membranes in an ultraviolet chamber.

Recomposition of the complex starting from the purified sub-units

Sub-units A and B spontaneously form a complex having a dissociation constant in the order of $10^{-10}$ M and same is completed within the first minute after mixture.

9. PREPARATION OF THE SAMPLES FOR THERAPEUTIC USE

The preparation can be made following commercial techniques, such as liquid formulations in aqueous vehicles having the usual additives (i.e., physiological solutions), solutions or emulsions eventually with other medicaments such as local analgesics.

The active crotoxin ingredient of the pharmaceutical compositions of the present invention exhibits excellent cytotoxic activity when administered in amounts ranging from about 1 mg to about 10 mg per ml of solution. A preferred dosage regiment for optimum results would be from about 1 mg to about 2 mg per ml of solution. The active compound may be administered in a convenient manner such as by intraperitoneal, intravenous (where water soluble), intramuscular or subcutaneous routes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile filtered solution thereof.

As used herein, "pharmaceutically acceptable carrier" includes any and all solvents, dispersion media, coatings, antibacterial and antifungal agents, isotonic and absorption delaying agents, and the like, the use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is used in effective amounts with a suitable pharmaceutically acceptable carrier in dosage unit form as hereinbefore disclosed. A unit dosage form can, for example, contain the principal active compound in amounts ranging from about 0.1 to about 100 mg. One means of parenteral use is by delivery with disposable sterile insulin syringe (0–40 units, with one unit corresponding to 0.025 or 0.05 mg of crotoxin) or a tuberculine syringe (0.1 ml corresponding to 0.1 or 0.2 mg crotoxin). Typically, the treatment can start with the daily administration of 0.1 mg with increases of 0.05-0.1 mg each three days up to a maximum of 0.5-0.6 mg a day and is continued for 2-3 months, depending on the tolerance and the clinical response. For combined use with crotoxin, cardiotoxin can be used in a concentration range of from about 0.01 mg to about 0.10 mg of cardiotoxin per 0.1 mg of crotoxin, with 0.05 mg of cardiotoxin being preferred. This can be properly delivered with a sterile disposable insulin syringe (0-40 units, one unit corresponding 0.0125 mg of cardiotoxin) or a tuberculine syringe (0.1 ml corresponding to 0.05 mg of cardiotoxin). In the case of compositions containing supplementary active ingredients, the dosages are determined by reference to the usual dose and manner or administration of the said ingredients.

CONCLUSIONS

Considering the results obtained using crotoxin complex for treating advanced cancer patients, the following conclusions can be formulated:

a. That cytotoxic action is related to the preferential disassociation of the crotoxin complex thus allowing the interaction of crotoxin B with the membranes of tumoral cells.

b. That crotoxin is active in several types of cancer metastases.

c. That no serious acute toxic effects are produced and no toxic effects either sub-acute or chronically accumulative are observed.

d. That, at therapeutic dosages, secondary or collateral effects are scarce and disappear 4 to 6 hours after administration.

e. That crotoxin does not require binding to plasma proteins for transport.

f. That therapeutic effect does not depend on a high plasma level.

g. That there is no accumulation in any organ.

h. That no toxicity which should be attributed to tumoral lysis, including but not limited to, hyperuricemia and/or hypercalcemia, has been observed.

i. That there are no contraindications.

j. That, according no clinical experiences with patients receiving several treatments, the crotoxin complex does not interact with other anti-tumor agents.

k. That crotoxin complex exhibits a large analgesic effect.

l. That crotoxin complex is poorly antigenic in either animals and humans.

m. That the final metabolites of the crotoxin complex integrate the amino acid pool.

n. That no psycho-organic dependency has been detected.

o. That administration is daily, does not require special technique or application procedure, and can be carried out in ambulatory conditions.

While the invention has been described in some detail by way of illustration and example, changes in form and the substitution or equivalents are contemplated as circumstances may suggest or render expedient. Although specific terms have been employed herein, they are intended in a descriptive sense and not for purposes of limitation.

What is claimed is:

1. A pharmaceutical composition for the treatment of malignant tumors which consists of a therapeutically effective amount of a crotoxin complex and a carrier, said crotoxin complex being comprised of an effective molar ratio of Crotoxin A to Crotoxin B, which composition is otherwise free of components of Crotalus durissus terrificus venom.

2. A pharmaceutical composition for the treatment of malignant tumors which comprises as the active ingredient a therapeutically effective amount of a crotoxin complex, said crotoxin complex being comprised of an effective molar ratio of Crotoxin A to Crotoxin B, which composition is free of other components of Crotalus durissus terrificus venom, wherein said complex is the sole neurotoxin present in said composition.

3. The pharmaceutical composition of claim 1 or claim 2 wherein said molar ratio of Crotoxin A to Crotoxin B is at least 1:1.

4. The pharmaceutical composition of claim 1 or claim 2 wherein the molar ratio of Crotoxin A to Crotoxin B is 1:1.

5. A method of treating a host having malignant tumors which comprises administering to said host an anti-tumor effective amount of a pharmaceutical composition which comprises as the active ingredient a therapeutically effective amount of a crotoxin complex, said crotoxin complex being comprised of an effective molar ratio of Crotoxin A to Crotoxin B, which composition is otherwise free of components of Crotalus durissus terrificus venom.

6. A method for treating a host having malignant tumors which comprises parenterally administering to said host an anti-tumor effective amount of a cytotoxic agent comprising a complex of crotoxin subunits A and B and which is free of other components of Crotalus durissus terrificus venom.

7. The method of claim 5 wherein said complex is the complex of Crotoxin A and Crotoxin B at a molar ratio of at least 1:1.

* * * * *